(12) United States Patent
Lonky et al.

(10) Patent No.: US 11,213,664 B2
(45) Date of Patent: Jan. 4, 2022

(54) FRICTIONAL TRANS-EPITHELIAL TISSUE DISRUPTION COLLECTION APPARATUS AND METHOD OF INDUCING AN IMMUNE RESPONSE

(71) Applicant: HISTOLOGICS, LLC, Anaheim, CA (US)

(72) Inventors: Neal Marc Lonky, Yorba Linda, CA (US); Martin L Lonky, Rancho Palos Verdes, CA (US)

(73) Assignee: Histologics, LLC, Yorba Linda, CA (US)

( * ) Notice: Subject to any disclaimer, the term of this patent is extended or adjusted under 35 U.S.C. 154(b) by 28 days.

(21) Appl. No.: 16/371,027

(22) Filed: Mar. 31, 2019

(65) Prior Publication Data

US 2019/0224463 A1    Jul. 25, 2019

Related U.S. Application Data

(60) Division of application No. 15/603,374, filed on May 23, 2017, now Pat. No. 10,258,780, which is a
(Continued)

(51) Int. Cl.
*A61B 10/02* (2006.01)
*A61M 37/00* (2006.01)
(Continued)

(52) U.S. Cl.
CPC ......... *A61M 37/0015* (2013.01); *A61B 10/02* (2013.01); *A61B 10/0291* (2013.01);
(Continued)

(58) Field of Classification Search
CPC ............ A61B 2010/0216; A61B 10/02; A61B 10/0291; A61B 2017/320004; A61B 2017/320008; A61B 2017/320012
See application file for complete search history.

(56) References Cited

U.S. PATENT DOCUMENTS

| 1,795,500 | A | 3/1931 | Omundson |
| 2,675,572 | A | 4/1954 | Nomiya |

(Continued)

FOREIGN PATENT DOCUMENTS

| AT | 392411 | 5/1988 |
| CH | 653880 | 1/1986 |

(Continued)

OTHER PUBLICATIONS

Blute, Renal brush biopsy: Survey of indications, techniques and results, J Urol., Aug. 1981, vol. 126(2), pp. 146-149.
(Continued)

*Primary Examiner* — Devin B Henson
*Assistant Examiner* — H. Q. Nguyen
(74) *Attorney, Agent, or Firm* — Sci-Law Strategies PC

(57) ABSTRACT

The invention relates to trans-epithelial frictionally abrasive tissue sampling devices for performing biopsies and methods of inducing an immune response against a pathogen, wherein epithelial cells containing the pathogen are disrupted with the frictionally abrasive tissue sampling device to introduce the pathogen into the bloodstream of a patient.

**14 Claims, 8 Dr

Related U.S. Application Data division of application No. 15/208,603, filed on Jul. 12, 2016, now Pat. No. 9,687,642, which is a continuation of application No. 14/602,002, filed on Jan. 21, 2015, now Pat. No. 9,393,394, which is a division of application No. 14/154,447, filed on Jan. 14, 2014, now abandoned, which is a division of application No. 12/669,638, filed as application No. PCT/US2008/070341 on Jul. 17, 2008, now Pat. No. 8,652,067.

(60) Provisional application No. 60/950,280, filed on Jul. 17, 2007.

(51) Int. Cl.
*A61B 10/04* (2006.01)
*A61B 17/32* (2006.01)

(52) U.S. Cl.
CPC ...... *A61B 10/04* (2013.01); *A61B 2010/0216* (2013.01); *A61B 2017/320004* (2013.01); *A61B 2017/320012* (2013.01); *A61M 2037/0023* (2013.01); *A61M 2037/0046* (2013.01); *A61M 2037/0061* (2013.01); *A61M 2202/206* (2013.01); *A61M 2202/30* (2013.01)

(56) References Cited

U.S. PATENT DOCUMENTS

| | | |
|---|---|---|
| 2,701,559 A | 2/1955 | Cooper |
| 2,717,437 A | 9/1955 | De Mestral |
| 2,811,969 A | 11/1957 | Shubert |
| 2,839,049 A | 6/1958 | Maclean |
| 2,847,005 A | 8/1958 | Bourne |
| 2,955,591 A | 10/1960 | Maclean |
| 3,018,498 A | 1/1962 | Wasserman |
| 3,263,681 A | 8/1966 | Nechtow |
| 3,511,242 A | 5/1970 | Agnone |
| 3,554,185 A | 1/1971 | Kohl |
| 3,559,226 A | 2/1971 | Burns |
| 3,628,522 A | 12/1971 | Kato |
| 3,774,590 A | 11/1973 | McDonald |
| 3,777,743 A | 12/1973 | Binard |
| RE27,915 E | 2/1974 | Kohl |
| 3,796,211 A | 3/1974 | Kohl |
| 3,877,464 A | 4/1975 | Vermes |
| 3,945,372 A | 3/1976 | Milan |
| 3,995,629 A | 12/1976 | Patel |
| 4,016,865 A | 4/1977 | Fredericks |
| 4,061,146 A | 12/1977 | Baehr |
| 4,127,113 A | 11/1978 | Nollan |
| 4,168,698 A | 9/1979 | Ostergard |
| 4,227,537 A | 10/1980 | Suciu |
| 4,245,653 A | 1/1981 | Weaver |
| 4,384,587 A | 5/1983 | Milgrom |
| 4,396,022 A | 8/1983 | Marx |
| 4,430,076 A | 2/1984 | Harris |
| 4,465,072 A | 8/1984 | Taheri |
| 4,467,816 A | 8/1984 | Schluter |
| 4,620,548 A | 11/1986 | Hasselbrack |
| 4,641,662 A | 2/1987 | Jaicks |
| D289,926 S | 5/1987 | Lonky |
| 4,700,713 A | 10/1987 | Kist |
| 4,754,764 A | 7/1988 | Bayne |
| 4,757,826 A | 7/1988 | Abdulhay |
| 4,759,376 A | 7/1988 | Stormby |
| 4,762,133 A | 8/1988 | Bayne |
| 4,763,669 A | 8/1988 | Jaeger |
| 4,777,947 A | 10/1988 | Zwick |
| 4,781,202 A | 11/1988 | Janese |
| 4,872,243 A | 10/1989 | Fischer |
| 4,873,992 A | 10/1989 | Bayne |
| 4,892,831 A | 1/1990 | Wong |
| 4,932,857 A | 6/1990 | Nishino |
| 4,946,389 A | 8/1990 | Weissenberger |
| 4,951,684 A | 8/1990 | McMillan |
| 4,961,430 A | 10/1990 | Sheahon |
| 4,965,725 A | 10/1990 | Rutenberg |
| 5,022,408 A | 6/1991 | Mohajer |
| 5,067,195 A | 11/1991 | Sussman |
| 5,069,224 A | 12/1991 | Zinnanti, Jr. |
| 5,092,345 A | 3/1992 | Sakita |
| 5,133,361 A | 7/1992 | Cox |
| 5,154,694 A | 10/1992 | Kelman |
| 5,184,626 A | 2/1993 | Hicken |
| 5,191,899 A | 3/1993 | Strickland |
| 5,195,964 A | 3/1993 | Kletzky |
| 5,197,949 A | 3/1993 | Angsupanich |
| 5,250,061 A | 10/1993 | Michelson |
| 5,253,652 A | 10/1993 | Fast |
| 5,257,182 A | 10/1993 | Luck |
| 5,259,391 A | 11/1993 | Altshuler |
| 5,287,272 A | 2/1994 | Rutenberg |
| 5,315,740 A | 5/1994 | Provost |
| 5,329,938 A | 7/1994 | Lonky |
| 5,370,128 A | 12/1994 | Wainwright |
| 5,421,346 A | 6/1995 | Sanyal |
| 5,445,164 A | 8/1995 | Worthen |
| 5,456,265 A | 10/1995 | Yim |
| 5,462,063 A | 10/1995 | Kist |
| 5,464,409 A | 11/1995 | Mohajer |
| 5,470,308 A | 11/1995 | Edwards |
| 5,476,104 A | 12/1995 | Sheahon |
| 5,535,756 A | 7/1996 | Parasher |
| 5,544,650 A | 8/1996 | Boon |
| 5,549,563 A | 8/1996 | Kroner |
| 5,623,941 A | 4/1997 | Hedberg |
| 5,643,307 A | 7/1997 | Turkel |
| 5,649,943 A | 7/1997 | Amoils |
| 5,713,369 A | 2/1998 | Tao |
| 5,722,423 A | 3/1998 | Lind |
| 5,738,109 A | 4/1998 | Parasher |
| 5,761,760 A | 6/1998 | Dumler |
| 5,785,785 A | 7/1998 | Chesley |
| 5,792,160 A | 8/1998 | Weiss |
| 5,800,362 A | 9/1998 | Kobren |
| 5,807,282 A | 9/1998 | Fowler |
| 5,857,982 A | 1/1999 | Milliman |
| 5,865,765 A | 2/1999 | Mohajer |
| 5,868,509 A | 2/1999 | Crutcher |
| 5,868,668 A | 2/1999 | Weiss |
| 5,899,850 A | 5/1999 | Ouchi |
| 5,913,857 A | 6/1999 | Ritchart |
| 5,916,228 A | 6/1999 | Ripich |
| 5,937,870 A | 8/1999 | Gueret |
| 5,951,550 A | 9/1999 | Shirley |
| 6,053,877 A | 4/2000 | Banik |
| 6,110,130 A | 8/2000 | Kramer |
| 6,132,421 A | 10/2000 | Clapham |
| 6,193,674 B1 | 2/2001 | Zwart |
| 6,258,044 B1 | 7/2001 | Lonky |
| 6,297,044 B1 | 10/2001 | Eisen |
| 6,336,905 B1 | 1/2002 | Colaianni |
| 6,346,086 B1 | 2/2002 | Maksem |
| 6,376,905 B2 | 4/2002 | Hisano |
| 6,379,315 B1 | 4/2002 | Claren |
| 6,387,058 B1 | 5/2002 | Wallach |
| 6,394,966 B1 | 5/2002 | Gill |
| 6,408,492 B1 | 6/2002 | Sparks |
| 6,494,845 B2 | 12/2002 | Rutenberg |
| 6,595,947 B1 | 7/2003 | Mikszta |
| 6,676,609 B1 | 1/2004 | Rutenberg |
| 6,730,085 B2 | 5/2004 | George |
| 6,740,049 B2 | 5/2004 | Wallach |
| 6,790,654 B2 | 9/2004 | Malinge |
| 6,860,738 B2 | 3/2005 | Bachmann |
| 7,004,913 B1 | 2/2006 | Rutenberg |
| 7,137,956 B2 | 11/2006 | Nishtalas |
| 7,156,814 B1 | 1/2007 | Williamson, IV |
| 7,157,233 B2 | 1/2007 | Fischer |
| 7,413,551 B2 | 8/2008 | Decker |
| 7,517,323 B2 | 4/2009 | Ng |
| D605,407 S | 12/2009 | Wagner |

(56) References Cited

U.S. PATENT DOCUMENTS

| | | |
|---|---|---|
| 7,749,173 B2 | 7/2010 | Larkin |
| 7,836,539 B2 | 11/2010 | Moskovich |
| 7,871,574 B2 | 1/2011 | Peltier |
| 8,152,739 B1 | 4/2012 | McCully |
| 8,348,856 B1 | 1/2013 | Malanowska |
| 8,439,847 B2 | 5/2013 | Larkin |
| 8,517,956 B1 | 8/2013 | Malanowska |
| 8,617,183 B2 | 12/2013 | Schneider |
| 8,652,067 B2 | 2/2014 | Lonky |
| 8,795,197 B2 | 8/2014 | Lonky |
| 9,028,484 B2 | 5/2015 | Craig |
| 9,044,213 B1 | 6/2015 | Lonky |
| 9,282,950 B2 | 3/2016 | Klein |
| 9,282,951 B2 | 3/2016 | Lonky |
| 9,393,394 B2 | 7/2016 | Lonky |
| 9,421,346 B2 | 8/2016 | Callahan |
| 9,687,642 B2 | 6/2017 | Lonky |
| 9,895,140 B1 | 2/2018 | Lonky |
| 10,201,332 B1 | 2/2019 | Lonky |
| 10,258,780 B2 | 4/2019 | Lonky |
| 2001/0022063 A1 | 9/2001 | Korteweg |
| 2002/0068881 A1 | 6/2002 | Kobren |
| 2002/0165467 A1 | 11/2002 | Rutenberg |
| 2003/0055373 A1 | 3/2003 | Sramek |
| 2003/0109804 A1 | 6/2003 | Auerbach |
| 2004/0029658 A1 | 2/2004 | Howe |
| 2004/0120989 A1 | 4/2004 | Vadas |
| 2004/0116827 A1 | 6/2004 | Tiberio |
| 2004/0138642 A1 | 7/2004 | Fischer |
| 2004/0181170 A1 | 9/2004 | Wallach |
| 2004/0181185 A1 | 9/2004 | Lee |
| 2004/0220478 A1 | 11/2004 | Wallace |
| 2004/0236247 A1 | 11/2004 | Rizvi |
| 2004/0260199 A1 | 12/2004 | Hardia |
| 2004/0260201 A1 | 12/2004 | Mueller |
| 2004/0267191 A1 | 12/2004 | Gifford |
| 2005/0059905 A1 | 3/2005 | Boock |
| 2005/0074269 A1 | 4/2005 | Asselin |
| 2005/0085845 A1 | 4/2005 | Hilaire |
| 2005/0215920 A1 | 9/2005 | Isa |
| 2005/0251093 A1 | 11/2005 | Abou-Kansoul |
| 2005/0261603 A1 | 11/2005 | Witenberg |
| 2006/0052805 A1 | 3/2006 | Cwik |
| 2006/0122641 A1 | 6/2006 | Eberle |
| 2006/0200043 A1 | 9/2006 | Jannetty |
| 2007/0060839 A1* | 3/2007 | Richardson ............ A61B 10/04 600/570 |
| 2007/0093727 A1 | 4/2007 | Feuer |
| 2007/0135731 A1 | 4/2007 | Ward |
| 2007/0100335 A1 | 5/2007 | Fischer |
| 2007/0107155 A1 | 5/2007 | Kacher |
| 2007/0118947 A1 | 5/2007 | Lorenzo |
| 2007/0161042 A1 | 7/2007 | Zuk |
| 2007/0270715 A1 | 11/2007 | Ng |
| 2007/0282222 A1* | 12/2007 | Larkin ............... A61B 10/0045 600/569 |
| 2007/0282223 A1 | 12/2007 | Larkin |
| 2008/0188769 A1 | 8/2008 | Lu |
| 2008/0216763 A1 | 9/2008 | Ebert |
| 2008/0262384 A1 | 10/2008 | Wiederkehr |
| 2009/0012424 A1 | 1/2009 | Huschmand |
| 2009/0024155 A1 | 1/2009 | Lee |
| 2009/0043224 A1 | 2/2009 | Lundkvist |
| 2009/0112239 A1 | 4/2009 | To |
| 2009/0149860 A1 | 6/2009 | Scribner |
| 2009/0275859 A1 | 11/2009 | Kim |
| 2009/0326414 A1 | 12/2009 | Peltier |
| 2010/0011483 A1 | 1/2010 | Pinkart |
| 2010/0210968 A1 | 8/2010 | Lonky |
| 2010/0249649 A1 | 9/2010 | Larkin |
| 2011/0152881 A1 | 6/2011 | Conner |
| 2011/0172557 A1 | 7/2011 | Lonky |
| 2011/0268610 A1 | 11/2011 | Recknor |
| 2013/0066233 A1 | 3/2013 | Klein |
| 2013/0267870 A1 | 10/2013 | Lonky |
| 2014/0128773 A1 | 5/2014 | Lonky |
| 2014/0358158 A1 | 12/2014 | Einarsson |
| 2016/0100862 A1 | 4/2016 | Parys |
| 2017/0021151 A1 | 1/2017 | Lonky |
| 2017/0112477 A1 | 4/2017 | Benning |
| 2018/0035983 A1 | 2/2018 | Lonky |
| 2018/0296800 A1 | 10/2018 | Kato et al. |

FOREIGN PATENT DOCUMENTS

| | | |
|---|---|---|
| EP | 2166965 | 7/2008 |
| WO | WO2005084555 | 9/2005 |
| WO | WO2007101994 | 9/2007 |
| WO | WO2009012392 | 1/2009 |
| WO | WO2012125757 | 9/2012 |
| WO | WO2015134568 | 9/2015 |

OTHER PUBLICATIONS

Boon et al., "Confocal Sectioning of Thick, Otherwise Undiagnosable Cell Groupings in Cervical Smears" Acta Cytol., vol. 37, pp. 40-48 (1991).

Boon et al., "Exploiting the "Toothpick Effect" of the Cytobrush by Plastic Embedding of Cervical Samples" Acta Cytol., vol. 35, pp. 57-63 (1991).

Boon, "A model for quantitative follow-up studies of cervical lesions," Diagn Cytopathol., 1992, vol. 8(1), pp. 8-17.

Butler, B., "Kuper brush in the diagnosis of endometrial lesions," The Lancet, Dec. 1971, vol. 298(7739), pp. 1390-1392.

DeGirolami, "Histo-brush technic for endometerial tissue study," Obstet Gynecol., Dec. 1961, vol. 28(6), pp. 861-866.

Dowlatshahi et al., "Evaluation of brush cytology as an independent technique for detection of esophageal carcinoma" J Thoracic and Cardiovascular Surgery, vol. 89, No. 6, pp. 848-851, Jun. 1985.

Fennessy, "Transbronchial biopsy of peripheral lung lesions," Radiology, May 1967, vol. 88(5), pp. 878-882.

Firestone, "Needle lung biopsy, bronchial brushing and mediastinoscopy in Management of Chest Diseases," Calif Med., Sep. 1973, vol. 119(3), pp. 1-5.

Gahres et al., "Histo-brush technic for Endometrial Tissue Study", Obstet Gynecol vol. 28, pp. 861-866 (1966)—Front Page Only.

Goldstein, "Esophageal biopsy utilizing a flexible brush," Gastrointest Endosc., Aug. 1968, vol. 15(1), pp. 53-55.

Granqvist, "Colonoscopic biopsies and cytological exam in chronic ulcerative colitis," J Gastroenterology, Apr. 1980, vol. 15(3), pp. 283-288.

Hardwick, "Brush biopsy in the diagnosia of neoplasia in Bartlett's esophagus," Disease Esophagus, Oct. 1997, vol. 10(4), pp. 233-237.

Iaccarino, "Percutaneous intralesional brushing of cystic lesions of bone: a technical improvement of diagnostic cytology," Skelatal Radiol, 1990, vol. 19(3), pp. 187-190.

Johnsson, "Cytological brush techniques in malignant disease of the endometrium," Acta Obstet Gynecol Scand, Jan. 1968, vol. 47, issue 1, pp. 38-51.

Johnsson, "Cytological diagnosis of endometrial disorders with a brush technique," Acta Obstet Gynecol Scand., 1971, vol. 50(2), pp. 141-148.

Kovnat, "Bronchial brushing through the flexible fiberoptic bronchoscope in the diagnosis of peripheral pulmonary lesions," Chest, Feb. 1975, vol. 67(2), pp. 179-184.

Liu, "Transcervical chorionic villus biopsy with a brush," Prenat Diagn., Sep.-Oct. 1985, vol. 5(5), pp. 349-355.

Maksem, "Endometrial brush cytology of advanced postmenopausal endometrium..." Diagn Cytopathol., Nov. 1998, vol. 19(5), pp. 338-343.

Matsuda, "Bronchial brushing and bronchial biopsy: comparison of diagnostic accuracy and cell typing reliability in lung cancer," Thorax, Jun. 1986, vol. 41(6), pp. 475-479.

Meulman, "Predictions of various grades of cervical neoplasia on plastic-embedded cytobrush samples," Anal Quant Cytol Histol., Feb. 1992, vol. 14(1), pp. 60-72.

Mills, "Transcatheter brush biopsy of intravenous tumor thrombi," Radiology, Jun. 1978, vol. 127(3), pp. 667-670.

(56) References Cited

OTHER PUBLICATIONS

Morteza, "Brush and forceps biopsy of biliary ducts via percutaneous transhepatic catheterization," Radiology, Jun. 1980, vol. 135, pp. 777-778.
Moskowitz, "To brush or not to brush is there really a question?," Chest, Jun. 1971, vol. 59(6), pp. 648-650.
Mullins, "A new technique for transbronchial biopsy in infants and small children," Pediatr Pulmonol, Oct. 1995, vol. 20(4), pp. 253-257.
Payne, "Diagnostic accuracy of cytology and biopsy in primary bronchial carcinoma," Thorax, Jun. 1979, vol. 43(3), pp. 294-299.
Pipkorn, "A brush to harvest cells from the nasal mucosa for microscopic and biochemical analysis," J Immunol Methods, Aug. 9, 1988, vol. 112(1), pp. 37-42.
Portner, "New devices for biliary drainage and biopsy," Radiology, Jun. 1982, vol. 138, pp. 1191-1195.
Raney, "Detection of carcinoma of upper urinary tract with steerable brush biopsy," Urology, Jul. 1979, vol. 14(1), pp. 77-78.
Ravinsky, "Cytologic features of primary adenoid cystic carcinoma of the uterine cervix. A case report," Acta Cytol., Nov.-Dec. 1996, vol. 40(6), pp. 1304-1308.
Riise et al., "Bronchial brush biopsies for studies of epithelial inflammation in stable asthma and nonobstructive chronic bronchitis" Eur Respir J vol. 9, pp. 1665-1671 (1996).
Riise, "A bronchoscopic brush biopsy study of large airway mucosal pathology in smokers . . . " Eur Respir J., Apr. 1992, vol. 5(4), pp. 382-386.
Roth et al., "Cytologic Detection of Esophageal Squamous Cell . . . " Cancer, vol. 80, No. 11, Dec. 1, 1997.
Sanderson, "Use of a new controllable-tip brush with the flexible fiber bronchoscope," Chest, Jun. 1974, vol. 65(6), pp. 620-621.
Sheline, "Fluoroscopically guided retrograde brush biopsy in the diagnosis of transitional cell carcinoma of the upper urinary tract . . . " Am J Roentgenology, Sep. 1989, vol. 153(2), pp. 313-316.
Willson, "Bronchial brush biopsy with a controllable brush," Am J Roentgenology, Jul. 1970, vol. 109(3), pp. 471-477.
Zavala, "Use of Bronchofiberscope for bronchial brush biopsy: diagnostic results and comparison with other brushing techniques," Chest, Jun. 1973, vol. 63(6), pp. 889-892.
Zeppa, "A model for quantitative follow-up studies of cervical lesions," Diagn Cytopathol, 1992, vol. 8(1), pp. 8-17.
ISR of Application No. 08796246, PCT/US2008/70341 published as WO2009012392 dated Oct. 22, 2008, 6 pages.
Extended ESR of Application No. 08796246, PCT/US2008/070341, May 11, 2012, 6 pages.
Australian Patent Exam Report 20130806, dated Aug. 6, 2013, 5 pages.
Communication under Article 94 of U.S. Appl. No. 08/796,246, PCT/US2008/070341, dated Jun. 8, 2015, 5 pages.
Article 94(3) European Communication, Application No. 08796246, PCT/US2008/070341, dated Jul. 4, 2016, 4 pages.
International Search Report of PCT/US17/14190, published as WO2017/132051, dated Apr. 10, 2017, 13 pages.
Parasher V.K. and Huibregtse, K., Endoscopic retrograde wire-guided cytology of malignant biliary strictures using a novel scraping brush, Gastrointestinal Endoscopy, (1998) 48 (3) 288-290.
Extended ESR of Application No. 17744713.3, PCT/US2017/014190, Aug. 19, 2019, 7 pages.
International Preliminary Report on Patentability of PCT/US17/14190, published as WO2017/132051, dated Jul. 31, 2018, 7 pages.

\* cited by examiner

FRICTIONAL TRANS-EPITHELIAL TISSUE DISRUPTION COLLECTION APPARATUS AND METHOD OF INDUCING AN IMMUNE RESPONSE

PRIORITY CLAIM

This application is a divisional of (1) U.S. Utility application Ser. No. 12/669,638 filed Jan. 19, 2010, which issued as U.S. Pat. No. 8,652,067 on Feb. 18, 2014 and claims priority to (1) through (2) pending U.S. Utility application Ser. No. 15/603,374 filed May 23, 2017 which is a divisional of (1) and claims priority to (1) through (3) U.S. Utility application Ser. No. 15/208,603 filed Jul. 12, 2016 which issued as U.S. Pat. No. 9,687,642 on Jun. 27, 2017 which is a continuation of (4) U.S. Utility application Ser. No. 14/602,002 filed Jan. 21, 2015 which issued as U.S. Pat. No. 9,393,394 on Jul. 19, 2016 and which is a divisional of (5) U.S. Utility application Ser. No. 14/154,447 filed Jan. 14, 2014, abandoned, and which is a divisional of and claims priority to (1) which is the National Phase of (6) Patent Cooperation Treaty Application US08/70341 filed Jul. 17, 2008 which claims priority to (7) U.S. Provisional Application No. 60/950,280 filed Jul. 17, 2007. These applications (1)-(7) are herein expressly incorporated by reference in their entireties and for all purposes.

FIELD OF THE INVENTION

The invention relates to epithelial tissue sampling and collection devices for performing biopsies from lesions and anatomical landmarks at risk of neoplastic transformation, including but not limited to the squamo-columnar junction of the female cervix, methods of inducing an immune response against a pathogen and methods of trans-epithelial drug delivery.

DESCRIPTION OF THE RELATED ART

Previous devices include brushes with rigid bristles that puncture and shear epithelial surfaces (U.S. Pat. Nos. 5,535,756; 6,258,044; 6,376,905; 6,494,845 and 6,132,421), single metal or plastic curettes that extend in a parallel direction to the applicator handle and are much larger than the innovation (U.S. Pat. Nos. 4,641,662 and 6,730,085), scalpels or similar bladed sharp cutting tools (U.S. Pat. Nos. 5,857,982; 5,800,362; 3,774,590; 5,092,345; 4,061,146; 5,868,668; 6,053,877; 5,470,308; 7,137,956, 4,168,698 and 4,757,826; and U.S. Publication Nos. 2005/0059905 and 2007/0093727), or very large electrified metal loops used to produce excisional biopsies (U.S. Pat. Nos. 5,913,857 and 5,951,550). One device performs simultaneous brush cytology and scrape biopsy on structures with an organic duct (U.S. Pat. No. 5,535,756).

Human papillomaviruses (HPV) are responsible for many cutaneous and mucosal lesions. Some viral genotypes are considered to be the causal agents of cervical cancer. Natural genital HPV infection seems to be poorly immunogenic because of its nonproductive and non-inflammatory characteristics and also because of mechanisms developed by the virus to counteract the immune response.

SUMMARY OF THE INVENTION

A first aspect relates to a fabric for functionally abrading epithelial surfaces including a backing material and a plurality of fenestrated loops attached to the backing material, the loops having sufficient flexibility and rigidity to frictionally abrade the epithelial surfaces, wherein the loops are about 3 mm to about 25 mm in length, wherein the loops have a short hook end, and wherein the distance from the top of the loop to the bottom of the hook is less than 50% of the length of the loop.

A second aspect relates to an apparatus for obtaining a histological sample including a handle, a platform at a distal end of the handle, and a fabric for functionally abrading epithelial surfaces including a backing material and a plurality of fenestrated loops attached to the backing material (26).

A third aspect relates to a method of inducing an immune response against a pathogen that normally evades the immune system including disrupting epithelial cells containing the pathogen with a frictional trans-epithelial tissue disruption apparatus, and thereby introducing the pathogen, DNA fragments, proteins or antigenic material into the bloodstream of a patient to elicit an immune response.

A fourth aspect relates to a method of trans-epithelial drug delivery including disrupting tissue with a trans-epithelial tissue disruption apparatus and applying a drug to intra-epithelial and sub-epithelial spaces created by the disrupting tissue.

Figure 7A:
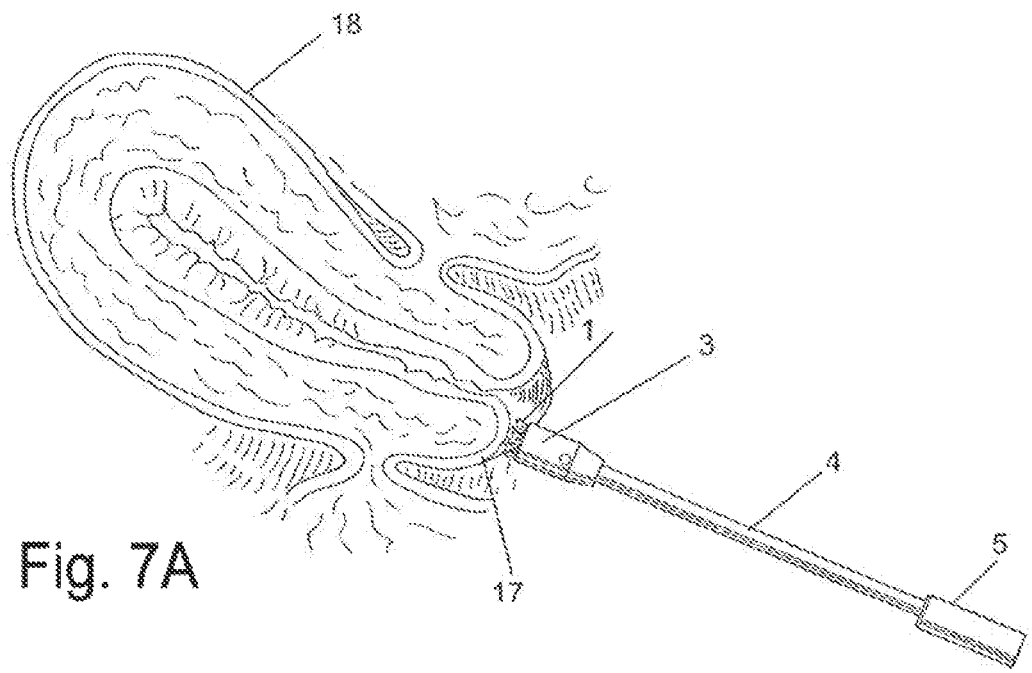
Figure 7B:
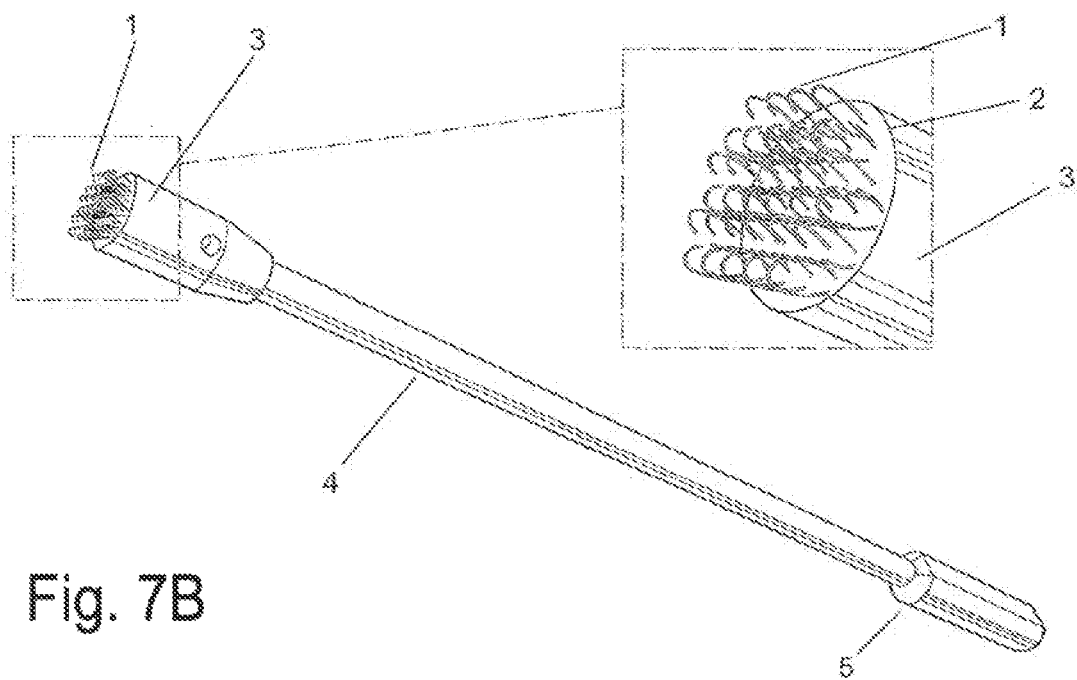
Figure 8A:
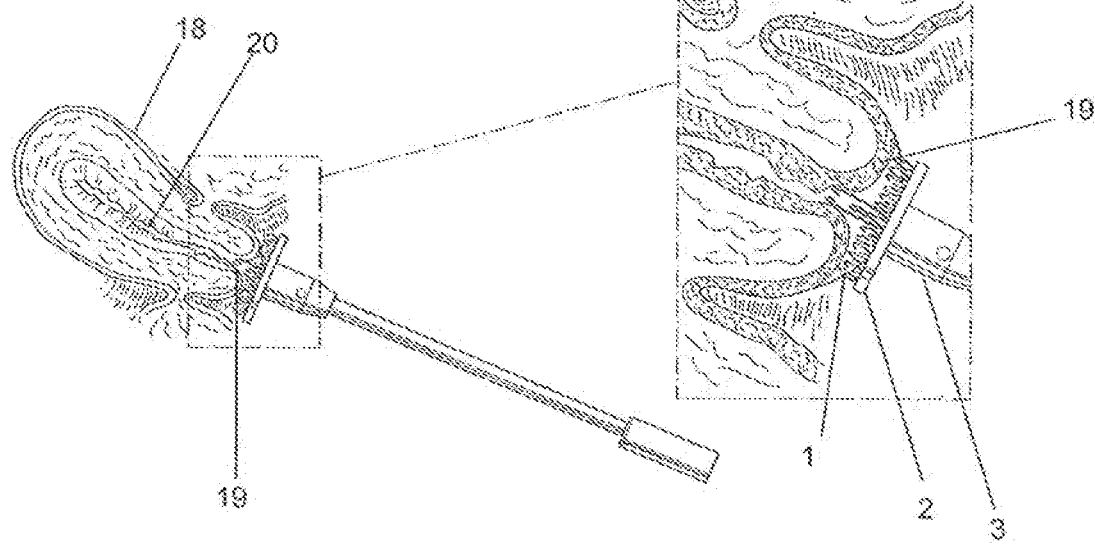
Figure 8B:
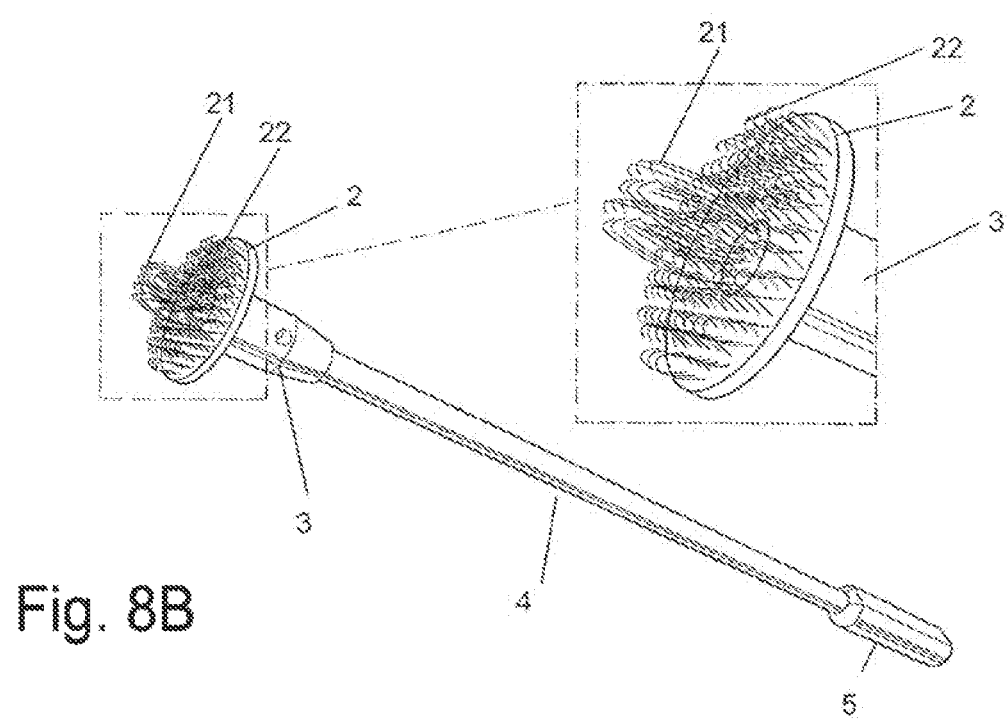

Schematic diagram of frictional trans-epithelial tissue disruption at the completion of the biopsy process, the collection of hooks arranged in rows create channels which collect and sequester the tissue and cell cluster fragments within the channels created in the device. When the device is removed from the epithelial surface, additional sample is captured and held due to the flexibility and recoil of the hooks;

FIG. 7(A). Side view of a focal biopsy apparatus, depicted at the outer lip of the cervix (exocervix); FIG. 7(B). Schematic diagram of apparatus for focal biopsies with an enlarged view of the platform and loops;

FIG. 8(A). Side view of apparatus for simultaneous biopsy of epithelial surfaces and canal-like surfaces. Longer central core fibers to insinuate into a canal and a perimeter of approximately 3 mm fibers contact an outer epithelial surface; FIG. 8(B). Schematic diagram of apparatus for simultaneous biopsy of epithelial surfaces and canal-like surfaces with enlarged view of platform and loops.

DETAILED DESCRIPTION OF THE PREFERRED EMBODIMENTS

Definitions

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated therewith.

The transitional phrase "consisting essentially of" limits the scope of a claim to the specified materials or steps and those that do not materially affect the basic and novel characteristic(s) of the claimed invention.

As used herein, the term "fenestrated loop" refers to a hooked, "candy-cane" shape formed by severing a loop, wherein a short, hooked end is less than about 50% of the length of the loop. In some embodiments, a fenestrated loop is formed by severing a loop once, leaving a short arm adjacent to the fenestrated loop.

Focal Biopsy

Some embodiments relate to a trans-epithelial, frictional tissue sampling and collection device to perform biopsies of lesions suspected of harboring disease. In some embodiments, a lesional biopsy site is no larger than about 10 mm in diameter (i.e., focal biopsy). In some embodiments the lesions are accessible to an examiner during routine examination. In other embodiments, the surface is accessible following entry into a body cavity through a natural orifice or surgical channel via a trochar and inspection using an endoscope with a biopsy port. The device head remains on the lesion or area of intended biopsy/therapy due to the rigid nature of the applicator. Referring to FIG. 7, a focal biopsy apparatus is configured with loops that are about 3 mm to about 25 mm in length, preferably about 3 mm in length, wherein the loops have a short hook end, wherein the distance from the top of the loop to the bottom of the hook is less than 50% of the length of the loop.

Regional Biopsy

In some embodiments, the intent is to biopsy and screen large geographic areas of tissue at risk for disease (e.g., neoplastic transformation such as, but not limited to, the squamo-columnar junction of the female cervix in the presence or absence of visualized lesions). The device provides samples of clumps or clusters of excavated epithelial tissue fragments for analysis, in contrast to other methods disclosed in prior art that provide surface and exfoliated cells by sweeping the cells from such target tissue sites, commonly with blunt spatula or soft bristle brush devices. The intent is to remove tissue based evidence with frictional biopsy of the larger area, which may range from 10-40 millimeters in diameter.

Simultaneous Biopsy of Epithelial Surfaces and Canal-Like Structures

In some embodiments, the device contains a central core of longer fenestrated loops (e.g., about 4-7 mm long), surrounded by a wider rim of shorter fenestrated loops (e.g., about 3 mm in length). The longer loops are geometrically suited to insinuate within a central canal structure, such as the endocervical canal of the cervix. There is simultaneously uniform contact of the fenestrated loop fibers circumferentially around the endocervical canal on the flat exocervical surface. With rotation and agitation in a back-and-forth motion, tissue is harvested within the fenestrated loop channels as described above.

In some embodiments, the device contains a central core of longer fenestrated loops (e.g., about 4-7 mm long), surrounded by a wider rim of shorter fenestrated loops (e.g., about 3 mm in length). The longer loops are geometrically suited to insinuate within a central canal structure, such as the endocervical canal of the cervix. There is simultaneously uniform contact of the fenestrated loop fibers circumferentially around the endocervical canal on the flat exocervical surface. With rotation and agitation in a back-and-forth motion, tissue is harvested within the fenestrated loop channels as described above.

Frictional Tissue Sampling and Collection Biopsy Devices

The frictional tissue sampling and collection biopsy devices disclosed herein utilize a fabric that includes minute plastic (e.g., nylon) fiber loops that are fenestrated at a minimal distance from the apex of the loop. The loops flex but do not fracture under minimal to moderate force or separate under pressure.

The semi-rigid loops may be pressed in a rotational manner (e.g., in sweeping or circular motion) away from or toward the operator, perpendicular, or at an angle into epithelial tissue surfaces. The semi-rigid loops remain flexible enough to cause separation of the fenestrated ends, creating frictional forces sufficient to cause local heating and buckling of the epithelial surface away from the underlying stroma. The loops are fenestrated such that with applied pressure they are flexible enough to open and provide access to a "collection well" for histological fragments. The tips of the fiber hooks are oriented away from the tissue. On pressing and rotation across the tissue surface, the fibers scrape, buckle and shear the epithelium from the underlying stroma. The fragments are excoriated from the tissue surface through the concomitant application of frictional forces applied to the tissue surfaces by the fenestrated loops. The frictional forces overcome the adhesive and binding forces of the tissue below to release fragments of various shapes and size, all eligible for collection in a histology lab, and subsequent processing and analysis.

The semi-rigid loops (e.g., made of nylon) hold the tissue fragments after excoriation because the loops are elastic enough to sufficiently re-close and capture the remove tissue. In addition, the spaces between the fibers also retain excoriated tissue. The frictional forces exceed the binding forces afforded by adhesion molecules which anchor epithelia to the basement membrane, as well as disrupting Van der Waals forces.

Once the epithelium is frictionally sheared from the underlying stroma, the tissue clumps and epithelial fragments are swept and excavated by the distal most curved apex of the loop and entrapped within the geometrically suited spaces between the closed, fenestrated loops. Thus, the method is frictional abrasion, excavation via rotation and other directional motion, and tissue collection within inter-loop channels.

The fabric can be cut into uniform shapes such as a circular disc or straight edge shape(s) and with uniform height, allowing the device to provide 360 degree coverage of tissue surfaces over suspected lesions, without a gap within the circumference of the device. This is in distinction to bristle brushes which are spiral or bent in shape, which present surface gaps that do not allow uniforms contact with the target tissue, and gaps that cause migration of the device from the lesion site toward the direction of rotation when such devices are pressed onto lesions and rotated or moved for tissue harvesting.

Following biopsy, the fabric, fibers, and/or device head (all with the tissue entrapped between the fibers) are removed and placed in a vial of liquid fixative for later laboratory work. A laboratory may remove the tissue from the device and process it for analysis. Therefore, one may intentionally design the device in an embodiment in which the user could easily decouple the device head from the device shaft. For example, some embodiments may have the shaft inserted into the head via a clip or screw thread mechanism, a key-in-lock design with a pressure release button, or a luer-lock type of attachment. Once the biopsy is obtained, the head and handle/shaft parts can be de-coupled, wherein the handle can be discarded, or sterilized and re-used, and the head immersed in a vial of fixative.

Some methods for removal of tissue from the fiber assembly include rinsing under pressure, immersion and agitation manually or mechanically, or by sonication. Alternatively, the fibers can be sheared from the fabric on telfa or other filter paper, and the fibers plucked off the paper leaving the entire biopsy specimen. Alternatively, after tissue is collected into the device channels, tissue may deposited via rotation or agitation in a vial of liquid fixative, rinsed off the device under pressurized spraying, or removed from the nylon fibers by cutting away the nylon fibers from the fabric (e.g., onto filter paper), thus leaving the tissue on the paper, which can be immersed in fixative.

In preferred embodiments, the fabric fibers are manufactured in a similar manner to Velcro® or other hook and pile type fastener, where strands are longer than conventional hook and pile, about 3 mm in length, fenestrated closer to the apex of the loop instead of close to the base of one arm of the loop, and thus appear V-wishbone shaped. They have a short hook end with the curvature starting at 2 mm from the base. Because the loop strands are longer, they flex and bend to a greater angle and twist with greater elasticity when rotated or agitated when compared with standard Velcro® Because the fenestration is closer to the base in standard Velcro®, the loops fenestrations are unlikely to separate, leaving the curved smooth surface of the loop in contact with the tissue, not providing sufficient frictional forces during rotation to shear and separate the epithelium form the underlying basement membrane and stroma.

Preferred embodiments utilize minute plastic fenestrated loops that are pressed perpendicular or at an angle into epithelial tissue surfaces which, upon rotational or agitational pressure forces, cause tissue epithelial fragments to be frictionally separated from the underlying tissue basement membrane and stroma. The channels between the fenestrated loops entrap and collect the tissue fragments. The process is similar to curettage with a blunt curved tool, which also scrapes, shears and strips epithelium from the underlying stroma of target tissues. On the other hand, the process is in contrast to sharp curettage where the purposefully sharp edge of the curette first incises, pierces, then shaves and scoops epithelium and underlying stroma from the tissue surface. The process described herein is less perceptible to patients than conventional biopsies and causes a smaller amount of blood loss and trauma.

In one aspect, the present invention relates to a frictional trans-epithelial tissue apparatus. In some embodiments, the apparatus comprises 3 mm or smaller loops adherent to and projecting perpendicular from a platform, with a density of 5-50 loops per square inch, evenly spaced or arranged in rows. The loops may be intact or fenestrated at the center or at their lateral aspect to allow for added flexibility and constructed from plastic, metal, or another stiff material. The rounded end of the loop is opposite the platform.

Loops of sufficient flexibility to withstand frictional forces and not fracture, and of sufficient tensile strength to generate sufficient frictional shear force during a sweeping or circular motion of the device to remove epithelium from tissue. The space between loops may serve to capture and harbor the sampled tissue.

In some embodiments designed for focal lesional biopsy, a flat, flexible platform, which anchors the loops may be of any size, but is most practically approximately 5-10 mm in diameter and circular in shape. The shape may be another geometrical design if it affords an advantage in covering the target tissue area for sampling. The platform may be hinged in such a way that it can be folded or compressed, inserted through a small endoscopic channel, and then reinstated to its original state as a platform with a sampling surface. It may be comprised of plastic, cloth, or another composite material. The loops are threaded through and project away from the platform towards the tissue surface. Some embodiments may comprise a hub fiber or "pin" that penetrates and anchors the center of the disc on the target biopsy area, serving as a central post to rotate the disc around for stability.

In other embodiments intended to screen a larger, regional tissue site at risk for neoplastic transformation or other disease process, the optimal shape is circular, the diameter could range from about 10-50 mm, and the loops project at varied distances from the platform to towards the tissue surface. For the purpose of histological screening to detect cervical neoplasia, the central 5 mm diameter disc projects longer (5-25 mm) fenestrated loop fibers, and is surrounded circumferentially by the aforementioned approximately 3-23 mm long loop fibers. The longer fibers insinuate inside canal structures, (e.g., the endocervical canal) simultaneously with contact of the shorter fibers with an outer endothelial surface (e.g., the exocervical surface). Upon pressure and rotation or agitation, the endocervical and exocervical tissues can be simultaneously frictionally sheared and collected. Histological screening may be necessary to correctly reflect the presence or absence of epithelial pathology, because adhesion molecules may prevent representative exfoliation from diseased tissue in some cases, leaving cytological screening methods lacking in accuracy.

Preferably, a frictional trans-epithelial biopsy sample is taken from a lesion or an anatomical region that is predisposed to disease.

Some embodiments comprise a plastic, metal, or mixed composition cylinder or curved convex head, which provides a flat surface for the platform to be attached to. It is equal or greater in diameter to the platform. The cylinder is 5-10 mm in length while the flat or convex base is less than about 3 mm thick.

Some embodiments comprise a rod or cylindrical shaped applicator probe comprised of any suitable material (e.g., wood, plastic, paper or metal), which has the base, platform and loop unit at its most distal end, wherein the applicator probe is approximately 2-5 mm in diameter and 15-30 cm in length. It is constructed larger or smaller depending on the access to the tissue surface. The shaft of the rod or cylindrical shaped applicator probe may be rigid or semi-rigid so as to not bow or arc when pressure is transmitted from the handle to the device head.

A handle into which the applicator probe can be transfixed is optionally mechanical, providing motorized rotational, drill-like movement or agitating vibration.

The device handle will be composed of stiff material, preferably plastic similar to Lucite, clear or opaque in coloration, rigid nylon plastic, or alternatively could be wood or metal. The device head can take may shapes, cylindrical or tapered in design, but the distal most platform face is circular, square, or polygonal, and may be composed of plastic, (e.g., nylon). The diameter may range from 5-50 mm. The fabric is welded to the nylon platform ultrasonically, or may alternatively be attached via adhesive, or via a rim or collar (e.g., which snaps on to the platform into a recess in the head of the device).

In some embodiments, the operator examines tissue surfaces and chooses an area to be sampled based on the presence of a suspicious lesion. In other embodiments, the operator chooses an anatomical landmark known to be "at risk" for neoplastic or disease transformation for the purposes of sampling the entire chosen surface.

The handle or applicator probe is grasped at its proximal end or handle.

The distal portion or head of the device that contains the base, platform and loops that project perpendicular from the base towards the tissue surface with the more rounded ends that are pressed against the tissue surface.

With moderate pressure, the examiner simultaneously presses and rotates the device against the tissue several times in a clockwise or counterclockwise direction, opening or separating the fenestrated loops, thus performing frictional disruption of the tissue surface. Alternatively, a sweeping motion may be used. If a motorized handle is used, it can be activated to assist in the rotation or vibration of the device.

The harvested tissue is collected from the tissue surface, and some tissue already trapped in the loops themselves is inspected and can be teased from the loops, or the loops transected from the fabric and separated, and the remaining tissue placed in a fixative solution.

Figure 1:
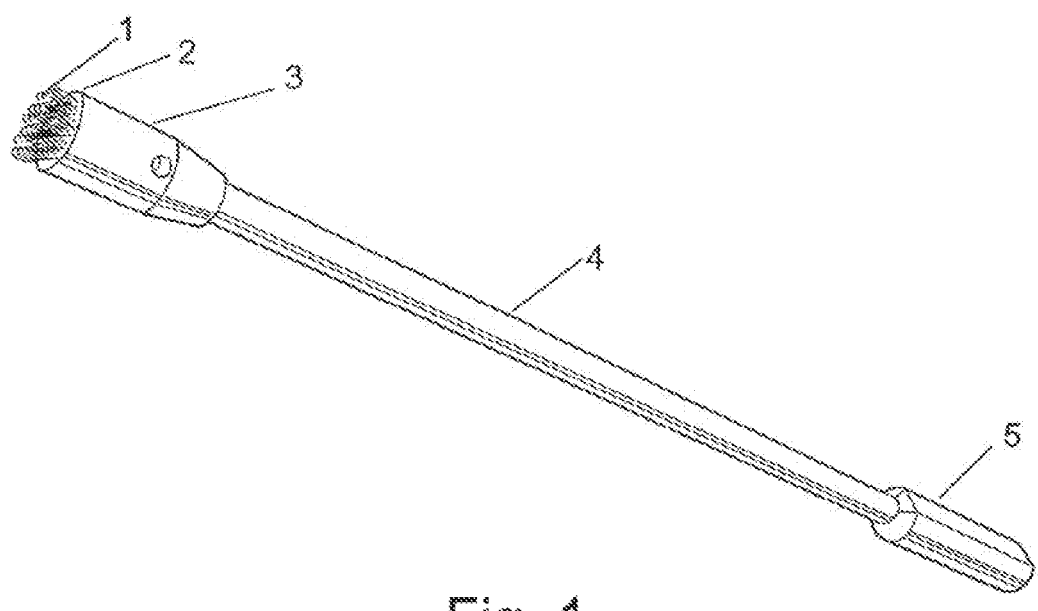
FIG. 1. Apparatus for frictional trans-epithelial tissue disruption of an epithelial flat surface.
Figure 3A:
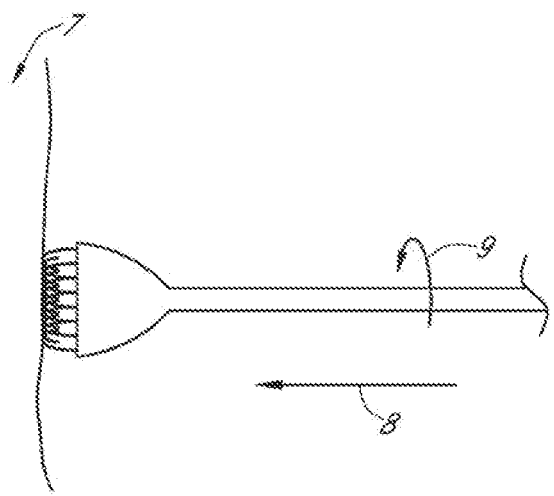
FIG. 3(A). Schematic diagram showing a method of frictional trans-epithelial tissue disruption of a flat epithelial surface.

As shown in FIG. 1, fabric with fenestrated loops (1) is connected to platform (2), which is in communication with head (3), located at a distal end of handle (5), optionally including an elongated rod (4). Referring to FIG. 3A, moderate force (8) is applied against a tissue surface (7). The device head is rotated (9) on the surface to frictionally separate or agitate the surface epithelium. The device head is rinsed or placed with tissue in the loops into fixative for subsequent pathological analysis.

Figure 2A:
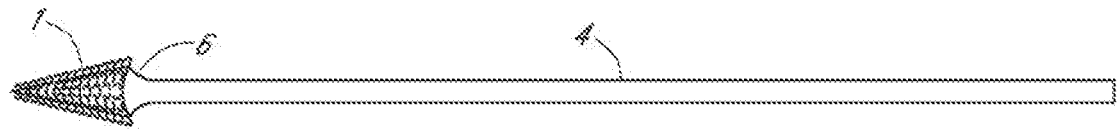
FIG. 2(A). Apparatus for frictional trans-epithelial tissue disruption of an epithelial-lined canal surface with tapered cone tip, Side view.
Figure 2B:
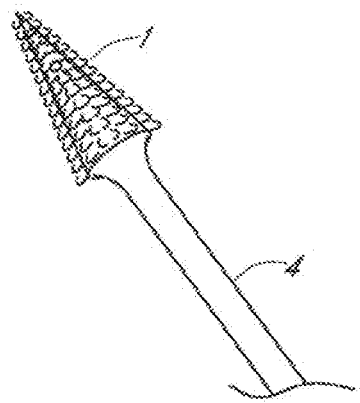
FIG. 2(B). apparatus for frictional trans-epithelial tissue disruption of an epithelial-lined canal surface with tapered cone tip, oblique view.
Figure 2C:
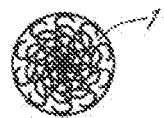
FIG. 2(C). apparatus for frictional trans-epithelial tissue disruption of an epithelial-lined canal surface with tapered cone tip, top view.
Figure 3B:
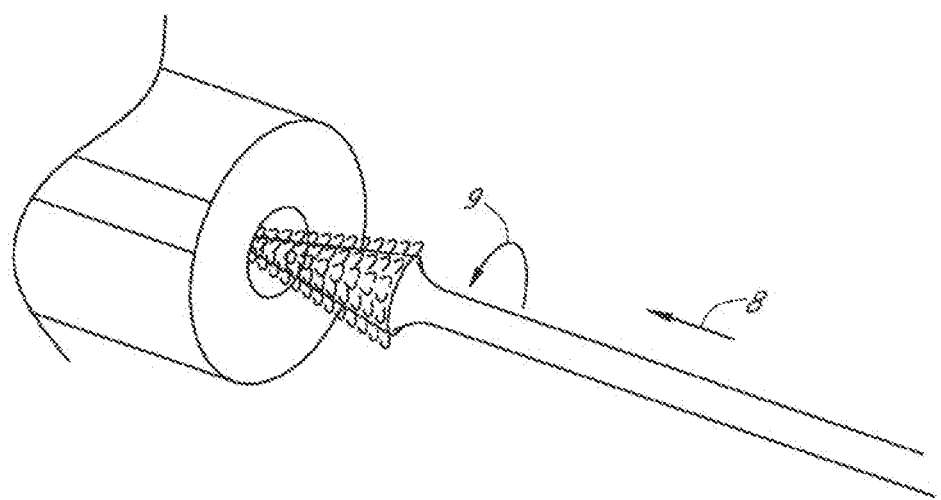
FIG. 3(B). schematic diagram showing a method of frictional trans-epithelial tissue disruption of an epithelial surface of a canal or body cavity.

An apparatus with a conical platform is depicted in FIG. 2. In FIG. 2A, fabric with fenestrated loops (1) is connected to conical platform (6). Referring to FIG. 3B, an apparatus with a conical platform may be inserted into a canal or cavity. The device head is rotated (9) while maintaining pressure force in direction (8). The device head with tissue in the loops is rinsed or placed into pathological fixative.

Figure 4:
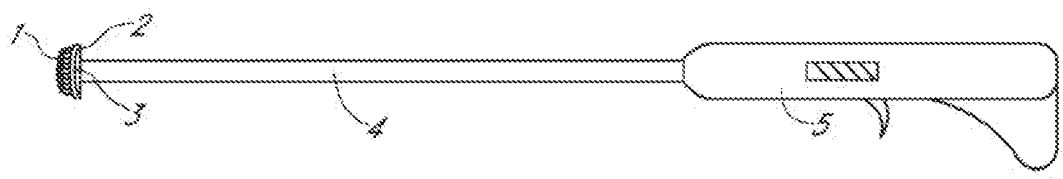
FIG. 4. Frictional trans-epithelial tissue disruptor with a motorized or vibratory handle used to spin or agitate the fenestrated loops.

An apparatus with a motor configured to rotate the platform is depicted in FIG. 4. Fabric with fenestrated loops (1) is attached to platform (2) on head (3) at the distal end of an elongated rod (4), which is attached to a motorized handle (5).

Figure 5:
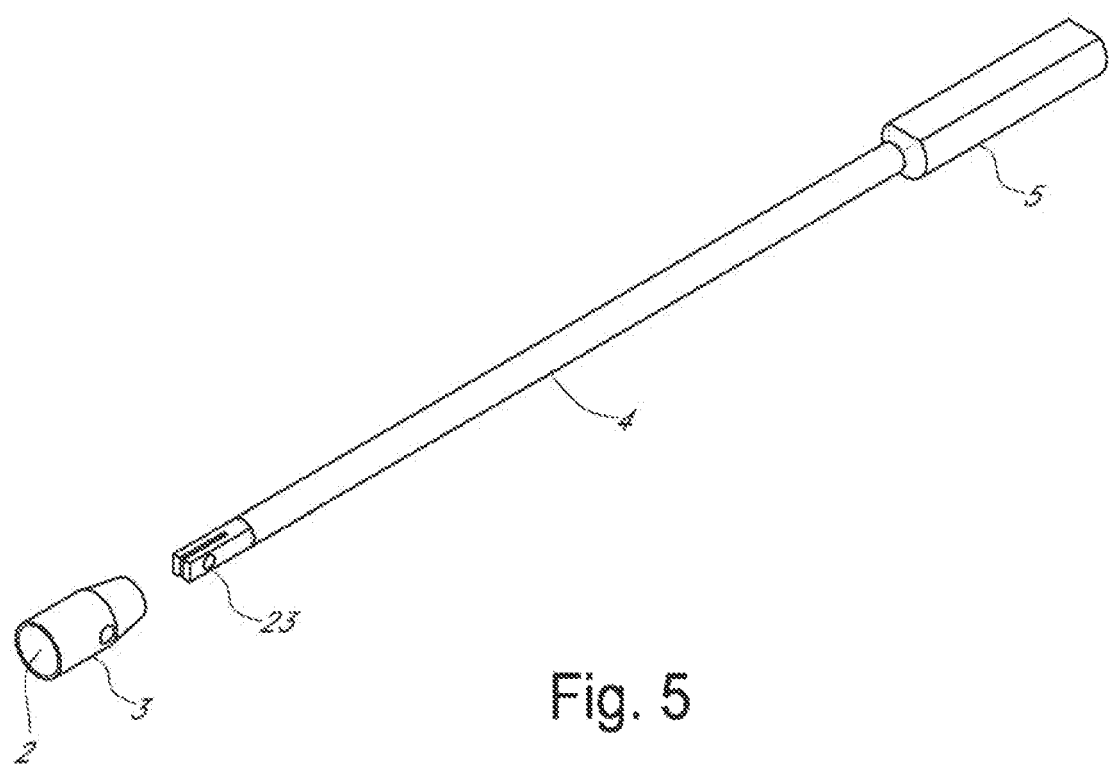
FIG. 5. Schematic diagram of an apparatus with a detachable platform that anchors fiber loops at a distal end of the handle.
Figure 6A:
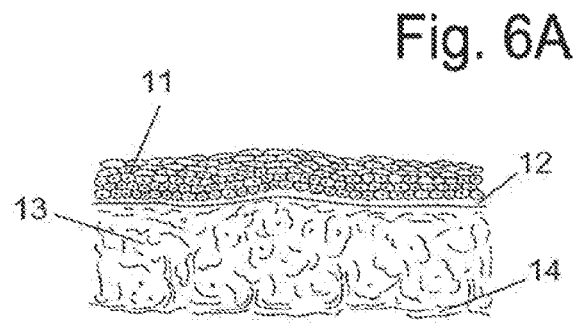
FIG. 6(A). Schematic diagram of frictional trans-epithelial tissue disruption showing representation of tissue with a squamous epithelial lined surface.
Figure 6B:
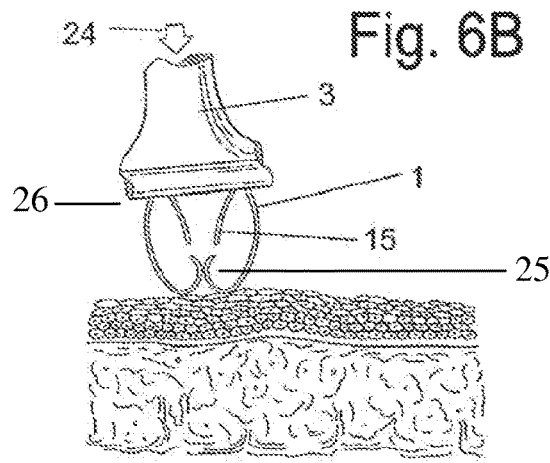
FIG. 6(B). Schematic diagram of frictional trans-epithelial tissue disruption with application of the frictional biopsy device to the body surface.
Figure 6C:
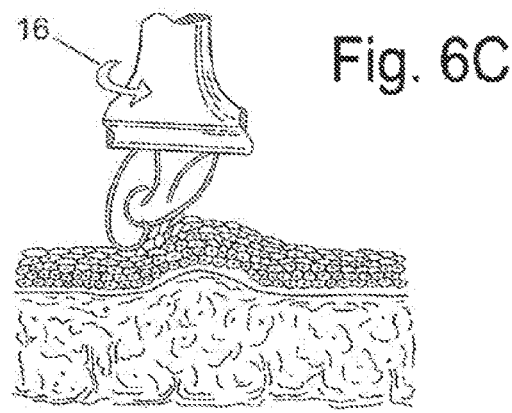
FIG. 6(C). Schematic diagram of frictional trans-epithelial tissue disruption where simultaneous pressure, agitational, and rotational force splays and separates the hooks/loops. Frictional abrasive forces create heat which buckles the epithelial surface.
Figure 6D:
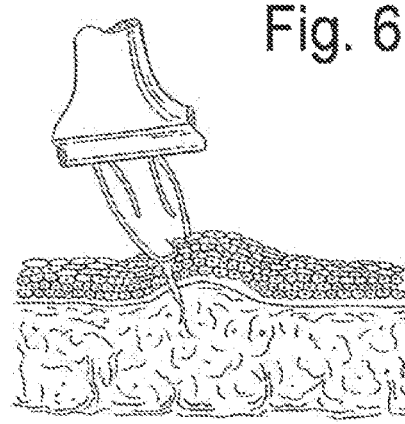
FIG. 6(D). Schematic diagram of frictional trans-epithelial tissue disruption where sufficient abrasion creates shearing and fracture of the epithelial surface at varying depths which could include fracture through the basement membrane into the subcutaneous layer.
Figure 6E:
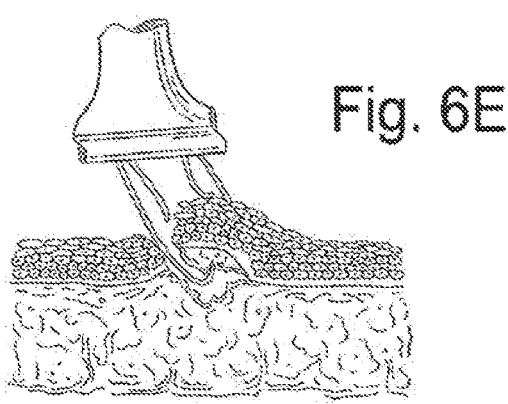
FIG. 6(E). Schematic diagram of frictional trans-epithelial tissue disruption where the hooks insinuate into the fracture plane, and with additional abrasive forces continue to shear the tissue fragments, while simultaneously retaining the tissue for capture and collection.
Figure 6F:
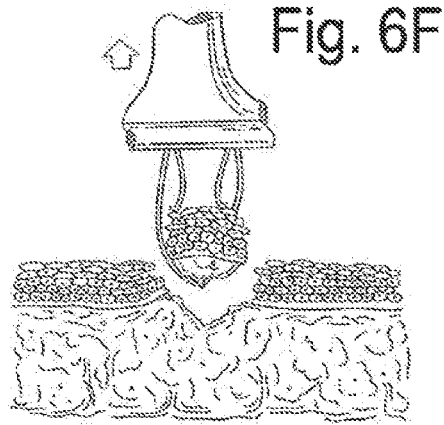
FIG. 6(F).

In some embodiments, the head is detachable from the elongated rod/handle. Referring to FIG. 5, a detachable head configuration allows the distal portion with head (3), platform (2), together with attached fabric containing loops, to be detached and placed into a preservative medium for later tissue removal and pathological processing. Some embodiments may have the shaft inserted into the head via a clip or screw thread mechanism, or a luer-lock type of attachment (23). Tissue fragments that remain attached to the detachable head are in addition to any free tissue obtained and collected from the tissue surface or the device as a result of the frictional tissue sampling.

Referring to FIG. 6, epithelial tissue samples are obtained by frictional trans-epithelial tissue disruption. A representation of tissue with a squamous epithelial lined surface is depicted in panel (A). The squamous epithelial multilayer (11) is shown with superficial flat and basal cuboidal epithelium. Basement membrane (12) separates the squamous epithelial multilayer from the subcutaneous tissue stroma (13) and the underlying sub-stromal tissue (14). FIG. 6B depicts application of the frictional biopsy device to the tissue surface. The device head (3) is applied (24) to a chosen area where curved portions of the fenestrated loops (1) press against the epithelial surface. A representation of two abutting hooks is shown, creating a collection channel. A shorter arm (15), adjacent to the fenestrated loop (1), may remain following severing of an initial continuous loop to create the fenestrated loop. In FIG. 6C, simultaneous pressure, agitational, and rotational force (16) splays and separates the hooks/loops. Frictional abrasive forces create heat which buckles the epithelial surface. Referring to FIG. 6D, sufficient abrasion creates shearing and fracture of the epithelial surface at varying depths which could include fracture through the basement membrane into the subcutaneous layer. As shown in FIG. 6E, the hooks insinuate into the fracture plane, and with additional abrasive forces continue to shear the tissue fragments, while simultaneously retaining the tissue for capture and collection. At the completion of the biopsy process (FIG. 6F), the collection of hooks arranged in rows creates channels that collect and sequester the tissue and cell cluster fragments within the channels. When the device is removed from the epithelial surface, additional sample collection is achieved due to the flexibility and recoil of the hooks.

Referring to FIG. 7A, frictional trans-epithelial tissue disruption with a focal biopsy apparatus is shown at the outer lip of the exocervix (17), alternatively known as the "transformation zone" of the cervix (18). In this configuration, fenestrated loops (1) approximately 3 mm in length are used to disrupt and collect tissue fragments. FIG. 7B depicts an enlarged focal biopsy apparatus, with an enlarged view of fenestrated loops (1) attached to platform (2).

Referring to FIG. 8A, simultaneous trans-epithelial biopsy of epithelial surfaces and canal-like surfaces, in particular, biopsy of the endocervical canal (20) and the exocervical area around the endocervical canal (i.e., the transformation zone) is shown (19). Referring to FIG. 8B, a central core of elongated loops of about 5-25 mm in length (21) are surrounded by a wider rim of shorter fenestrated loops of about 3-23 mm in length (22).

The frictional tissue sampling and collection device can be used on any body surface, both external to the body, body cavities, or on internal organs. To access epithelial surfaces of internal body organs, the device head may be deflated, folded or collapsed to pass through a small aperture or port, and re-opened or expanded to fully expose the fabric to the biopsy surface. This device can be used on humans or any other living organism with an epithelial surface. Any tissue surface may be sampled. The ease of use in each case will be related to the strength of the individual tissue adhesion and binding forces in specific locations. The loops themselves can harvest the tissue and also serve as tissue collection reservoirs for later storage once placed in a fixative medium. The platform with the loops may be detached from any applicator for later examination and processing (i.e., decoupled from the instrument used to press against tissue surfaces to obtain the tissue sample).

If the tissue surface is a canal or concave shaped area of the body, instead of a perpendicular platform design, the loops are directly attached to the probe itself which are gradually tapered at the end to facilitate insertion into the canal. The loops project perpendicularly from the probe surface at its distal end, and the unit, once placed into the canal that is lined on its surface with epithelium, contacts such epithelium snugly.

The loops can be mounted on the platform or project from the rim surface of the platform, perpendicular or at an angle to the platform along the margin of the platform, or attached to other delivery applicators, including the examiner's gloved finger, or other surgical instruments. The platform can be any shape or size which can fit on a tissue surface. The base assembly can be any shape or size, and may be permanently rigid or collapsible.

If the tissue surface lies within a canal shaped tissue surface, the loops can be attached directly to the applicator probe, which can be inserted into the canal shaped body cavity. The probe with the loops projecting from the surface and contacting the epithelium is rotated causing the frictional disruption sampling from the tissue surface. The shape of the probe can be constructed in any shape that allows a snug fit into the canal. The loops may be arranged in rows or equally spaced, allowing for maximal contact and tissue collection.

Some embodiments of the invention comprise a motorized mechanical assistance via a mechanical handle into which the most proximal end of the applicator probe is inserted. Such mechanical assistance may enhance the rotational or vibratory force that the device transmits to the tissue after contact is established. This can increase the frictional forces and the speed of the tissue disruption/sampling and shorten the procedure time.

Preferred Parameters of Fibers

The frictional sampling loops of the invention are collectively referred to as fenestrated loop fibers. In particularly preferred embodiments, the fibers are made using the hooked side of a modified Velcro® or other hook and pile type fastener, where the strands are about 3 mm in length and are V-wishbone shaped. They have a short hook end (25) with the curvature starting at 2 mm from the base. In various embodiments, the loops may be 2.5-25 mm in length, 3-5 mm in length, 3-10 mm in length, 3-15 mm in length, 3-20 mm in length or 3-25 mm in length.

In comparison, standard Velcro® is about 2 mm long and is more hooked. Thus, the loops of the present invention are longer than those of standard Velcro®, they are made of a similar nylon material compared with standard Velcro®, are more flexible when rubbed on a tissue surface due to their length, and they have shorter loops that hook nearer to the end of the strands. In particular, the distance from the top of the loop to the bottom of the hook is preferably less than 50% of the length of the loop, more preferably less than 40%, still more preferably less than 30%, and even more preferably less than 20% the length of the loop. This distance is also preferably at least 1% the length of the loop, more preferably at least 5% the length of the loop, and still more preferably at least 10% the length of the loop. Thus, the invention includes hooks in all of the ranges between any of the preferred minimum distances and any of the preferred maximum distances. The bottoms of the hooks are preferably arranged so that they are all approximately the same distance from the loop, although this is not strictly necessary. Because the hooks are cut at a relatively distal location, the ends of the hooks are more accessible to the tissue surface allowing for uniform transmission of frictional forces to the tissue surface. As a result, the action of the fibers more effectively buckle and shear the tissue, while the loops sweep over and capture the tissue.

In a preferred embodiment, the loop fibers are arranged so as to efficiently capture tissue. Thus, in one preferred embodiment, the fibers are arranged in an orderly orientation. For example, the fibers can be arranged in rows between which the tissue can be captured. The hooks can be arranged to be oriented at approximately the same angle and direction in each of the fibers. Thus, the fibers can be organized such they all have a consistent direction and angle of orientation. In addition, the spacing between each of the fibers can be made to be the same or different.

In use, the device can be oriented so that the fibers are perpendicular to tissue, and then pressure is applied. As a result, the epithelial surface is frictionally sheared. Thus, the fibers are preferably mounted on a flat or curved platform, optimally 4-10 mm in diameter so as optimize this process. However, alternatively shaped platforms can also be used in certain embodiments. Because the fibers can be mounted directly on the platform, which may be flat or slightly curved, the orientation remains evenly spaced and the spaces inside the fenestrated loops and between them remain evenly distributed to facilitate tissue capture.

In some embodiments the platform may in the form of a thumbtack, wherein it is attached to the handle. However, the platform and handle may take on a variety of forms. It is envisioned that the handle and the platform may be molded as one piece, and the fibers (e.g., modified Velcro®) may be attached with adhesive or via ultrasonic or thermal welding of the fabric to the platform.

Method of Inducing an Immune Response by Autoinoculation

In some embodiments, the trans-epithelial, frictional tissue sampling and collection devices described herein are utilized to agitate and disrupt epithelial cells containing a pathogen, or cellular proteins altered by a pathogen, to induce an immune response against the pathogen. This results in auto-inoculation of tissues that harbor pathogens and macromolecules such as virally altered DNA and/or oncogenic proteins. The method may also be termed therapeutic frictional abrasion-excoriation. This method is advantageous when a pathogen is normally able to evade an immune response. For example, some viruses remain in surface epithelial layers where they are sequestered from the immune system. Other viruses may be integrated into cellular DNA, thereby evading immune detection.

The methods of inducing an immune response against a pathogen that normally evades the immune system comprise the steps of a) disrupting epithelial cells containing the pathogen, virally altered DNA, or cellular oncoproteins with a micro-curettage device described herein, and b) introducing the pathogen into the bloodstream of a patient to elicit an immune response.

In some embodiments, the trans-epithelial, frictional tissue sampling and collection devices described herein are utilized to disrupt epithelial cells to induce an immune response against human papillomaviruses (HPVs). HPVs are persistent viruses that can remain in their hosts for long periods of time before causing any ill effects. Generally, the host reacts to viral pathogens by generating both humoral and cell-mediated responses. Humoral responses are typically antibody-mediated and involve the secretion of antibodies such as immunoglobulin A (IgA) and immunoglobulin G (IgG) by B lymphocytes. Cell-mediated responses, on the other hand, are carried out by immune effector cells such as dendritic cells (DCs), natural killer (NK) cells, macrophages and T lymphocytes which secrete a number of cytokines including interferons (INF) and tumor necrosis factor (TNF), and up-regulate the expression of Fas ligand (FasL) and TNF-related apoptosis inducing ligand (TRAIL) on their cell surface.

In the case of HPV infection, the immune response is frequently weak or undetectable, and accompanied by little or no inflammation. Even when an immune response is elicited, it may not be able to clear the virus. Disruption of the epithelial surface by frictional tissue disruption induces repair and inflammation and serves to auto-inoculate the patient. Without wishing to be bound by any theory, exposure of the epithelial surface to frictional tissue disruption, uniquely induced by the apparatus and methods disclosed herein through local heating from friction forces exerted, may enhance the induction of repair, inflammation and an immune response following patient autoinoculation. Agitation or scrubbing of a lesion serves to introduce viral particles into the bloodstream of a patient where they can trigger a humoral or antibody related immune response. In addition the method can fracture cells releasing antigens locally within the tissue stroma inducing a cell mediated response associated with the release of cytokines and attraction of helper and killer T cells to the sampled tissue area.

Advantageously, the method of the present invention auto-inoculates a patient with viral particles of the specific viral serotype(s) that the patient is infected with. In contrast, current vaccine strategies are effective on a subset of HPV strains. For example, GARDASIL® by Merck & Co., Inc. is indicated to help prevent cervical cancer, precancerous and low-grade cervical lesions, vulvar and vaginal pre-cancers and genital warts caused by human papillomavirus (HPV) types 6, 11, 16 and 18 and Cervarix™ by GlaxoSmithKline is an HPV 16/18 cervical cancer candidate vaccine. The vaccine is commonly injected in a limb, not the target organ at risk, the cervix, and has been only documented to elicit a humoral antibody immune reaction.

Drug Application

In some embodiments, an adjuvant drug or an immune modulating agent is used in combination with the autoinoculation method, thus augmenting an immune response. For example, Imiquimod (Aldara® topical cream, manufactured and marketed by Graceway Pharmaceutical Company) is approved for the treatment of actinic keratosis, external genital warts and superficial basal cell carcinoma (sBCC), a type of skin cancer. An immune response may be enhanced by using such immune modulating agents in combination with autoinoculation by the methods described herein. The adjuvant drug can be applied to the fenestrated loop fibers directly akin to toothpaste on a toothbrush, or a channel within the applicator can be used to transmit the drug from the top of the handle by means of a squeeze bulb or syringe, through a small lumen in the center of the fabric disc, concomitant with the tissue disruption, delivering drug into the fracture crevices created during the frictional buckling and shearing process created by the device.

Some embodiments comprise a method of drug delivery to a pathological lesion or areas of tissue that concomitantly disrupts tissue planes, creating crevices or pathways for drugs to enter via intra-epithelial and sub-epithelial spaces. This is in contrast to topical therapies, which are slowly absorbed into and through the epithelia. Intra-lesional application is more focused and requires less drug, presenting less risk of side effects.

Any type of drug (e.g., ablative, antibiotic, antiseptic, immune modulating, etc. may be used.

In some embodiments, drug is delivered via an applicator comprising a fabric with fenestrated loops as described herein. Drug is applied in a manner akin to applying toothpaste to a toothbrush, or drug may injected onto the platform or the apparatus via a channel leading through a hollow applicator handle. The drug application apparatus may optionally have an element through which the drug is delivered (e.g., a syringe with a locking mechanism). Drug is applied to a "wound" created by frictionally agitating the tissue. In some embodiments, the fenestrated loops may be impregnated with a drug during manufacture, wherein the drug leeches out into the disrupted tissue when the fiber contacts and macerates/disrupts the tissue.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

The invention claimed is:

1. A fabric for abrading epithelial surfaces and collecting a histological tissue sample comprising:
    a backing-material;
    a plurality of curved fenestrated loops comprising a short hook end and a first length attached to the backing material, where each curved fenestrated loop of the plurality of curved fenestrated loops is formed from each cut of a plurality of cuts on each loop of a plurality of loops at a distal location from the backing material, generating the curved fenestrated loop, where the first length is the distance from the top of the plurality of curved fenestrated loops to the backing material, where the plurality of curved fenestrated loops are arranged to form one or more channels, where the plurality of curved fenestrated loops have sufficient flexibility and rigidity to frictionally abrade an epithelial surface, where the first length is between 3 mm and 25 mm, where a distance from the top of the plurality of curved fenestrated loops to the bottom of the short hook end is less than twenty (20) percent of the first length, where rotation of the fabric pressed against the epithelial surface is adapted to abrade the epithelial surface with the short hook end adapted to release the histological tissue sample; and
    a plurality of curved short arms with a second length attached to the backing material, where the second length is less than the first length, where the plurality of curved short arms are formed from the plurality of cuts on the plurality of loops, where each curved short arm of the plurality of curved short arms is adjacent to each curved fenestrated loop of the plurality of curved fenestrated loops, where the histological tissue sample is adapted to collect in the plurality of curved short arms, where the plurality of curved fenestrated loops do not fracture or separate under moderate pressure, where under applied pressure when the fabric is pressed and rotated against the epithelial surface the short hook end of the plurality of curved fenestrated loops is adapted to splay and separate from the curved short arms thereby opening a collection well to collect the histological tissue sample.

2. The fabric of claim 1, where the backing material is adapted to be applied to a flexible platform.

3. The fabric of claim 1, where the short hook end is oriented towards the backing material.

4. The fabric of claim 1, where the plurality of curved fenestrated loops are made of plastic.

5. The fabric of claim 1, where the plurality of curved fenestrated loops are made of nylon.

6. A fabric for removing and collecting a histological tissue sample from an epithelial surface comprising:
    a backing material;
    a plurality of curved fenestrated loops attached to the backing material each with a first length and including a short hook end, where the plurality of curved fenestrated loops have sufficient flexibility and rigidity to remove, collect and store the histological tissue sample from the epithelial surface, where the first length is between 3 mm and 25 mm, where a distance from the top of the plurality of curved fenestrated loops to the bottom of the short hook end is less than 20% of the first length of the plurality of curved fenestrated loops, where rotation of the fabric pressed against the epithelial surface is adapted to abrade the epithelial surface with the short hook end adapted to release the histological tissue sample; and
    a plurality of curved short arms with a second length attached to the backing material, where the second length is less than the first length, where each curved short arm of the plurality of curved short arms is adjacent to each curved fenestrated loop of the plurality of curved fenestrated loops, where the curved fenestrated loops do not separate under minimal pressure, where under applied pressure when the fabric is pressed against the epithelial surface the short hook end of the plurality of curved fenestrated loops further separate from the curved short arms thereby providing a collection well formed between the curved short arms and the curved fenestrated loops for the histological tissue sample.

7. The fabric of claim 6, where the backing material is adapted to be applied to a flexible platform.

8. The fabric of claim 6, where the backing material is adapted to adhere to a rigid platform.

9. The fabric of claim 6, where the short hook end is oriented towards the backing material.

10. The fabric of claim 6, where the short hook end orients towards the epithelial surface under pressure.

11. The fabric of claim 6, where the short hook end under pressure applies frictional forces to the epithelial surface to excoriate the histological tissue sample.

12. The fabric of claim 6, where the backing material is adapted to be cut into uniform shapes.

13. A method for removing and collecting a histological tissue sample from an epithelial surface comprising:
    receiving a fabric attached to a platform, where the fabric includes a backing material adapted to be adhered to the platform and a plurality of curved fenestrated loops attached to the backing material having a length and sufficient flexibility and rigidity to remove and collect the histological tissue sample from the epithelial surface, where each of the plurality of curved fenestrated loops includes a short hook end, where the length is between 3 mm and 25 mm, where a distance from the top of the plurality of curved fenestrated loops to the bottom of the short hook end is less than 20% of the length of the plurality of curved fenestrated loops, where the fabric includes a plurality of curved short arms, where each curved fenestrated loop of the plurality of curved fenestrated loops is formed from each cut of a plurality of cuts at a distal location from the backing material generating the short hook end, where each curved short arm of the plurality of curved short arms is formed from each cut of the plurality of cuts at the distal location, where each curved short arm of the plurality of curved short arms is adjacent to each curved fenestrated loop of the plurality of curved fenestrated loops, where the fenestrated loops do not fracture under minimal pressure, where under pressure when the fabric is pressed against the epithelial surface, the short hook end of the plurality of curved fenestrated loops separates from the curved short arms;
    contacting the fabric to the epithelial surface;
    applying pressure to the fabric in contact with the epithelial surface; and
    rotating the platform clockwise and counterclockwise, where one or more short hook ends abrades the epithelial surface when rotated releasing the histological tissue sample, where the plurality of curved fenestrated loops and curved short arms collect the histological tissue sample.

14. The method of claim 13, where the short hook end applies frictional forces to the epithelial surface to excoriate the histological tissue sample under pressure.

* * * * *